US009066764B2

(12) United States Patent
Perez (10) Patent No.: US 9,066,764 B2
(45) Date of Patent: Jun. 30, 2015

(54) LONG BONE FIXATION SYSTEM AND METHODS

(75) Inventor: Edward A. Perez, Memphis, TN (US)

(73) Assignee: Campbell Clinic, P.C., Germantown, TN (US)

( * ) Notice: Subject to any disclaimer, the term of this patent is extended or adjusted under 35 U.S.C. 154(b) by 147 days.

(21) Appl. No.: 13/565,215

(22) Filed: Aug. 2, 2012

(65) Prior Publication Data

US 2013/0030435 A1    Jan. 31, 2013

Related U.S. Application Data

(63) Continuation of application No. 12/251,821, filed on Oct. 15, 2008, now abandoned.

(60) Provisional application No. 60/999,181, filed on Oct. 16, 2007.

(51) Int. Cl.
*A61B 17/58* (2006.01)
*A61B 17/72* (2006.01)

(52) U.S. Cl.
CPC .................................. *A61B 17/7233* (2013.01)

(58) Field of Classification Search
CPC . A61B 17/72; A61B 17/7233; A61B 17/7216
USPC ........................ 606/62–68, 70–71, 280–299
See application file for complete search history.

(56) References Cited

U.S. PATENT DOCUMENTS

| 5,603,715 A | 2/1997 | Kessler |
| 7,938,850 B2 | 5/2011 | Orbay et al. |
| 8,157,803 B1* | 4/2012 | Zirkle et al. ................ 606/64 |
| 2003/0097131 A1 | 5/2003 | Schon et al. |
| 2003/0135212 A1 | 7/2003 | Chow |
| 2006/0095039 A1 | 5/2006 | Mutchler |
| 2006/0100623 A1* | 5/2006 | Pennig ........................ 606/64 |
| 2007/0219636 A1 | 9/2007 | Thakkar |
| 2008/0154311 A1 | 6/2008 | Staeubli |
| 2008/0294164 A1 | 11/2008 | Frank et al. |
| 2010/0256685 A1 | 10/2010 | Plecko et al. |

* cited by examiner

*Primary Examiner* — Matthew Lawson
(74) *Attorney, Agent, or Firm* — Woodard, Emhardt, Moriarty, McNett & Henry LLP (57) ABSTRACT

A method of stabilizing a fractured bone includes: a) providing a first support member in a medullary canal of a fractured bone; b) providing a second support member outside the fractured bone; c) providing a transverse connector adapted to link the first support member to the second support member in an angle-stable connection; d) connecting the transverse connector to the first and second support members in an angle-stable connection; e) providing one or more bone screws adapted to be connected to the second support member in an angle-stable connection; and f) implanting the bone screws such that the shank of the screw is implanted in the fractured bone while the head of the screw is connected to the second support member in an angle-stable connection. The system provides superior fixation of long bones that allows for early functional range of motion without loss of alignment or fixation.

6 Claims, 7 Drawing Sheets

LONG BONE FIXATION SYSTEM AND METHODS

This application is a continuation of U.S. application Ser. No. 12/251,821, filed Oct. 15, 2008 now abandoned, which claims the benefit of U.S. Provisional Application No. 60/999,181, filed Oct. 16, 2007, and which is hereby incorporated by reference.

FIELD OF THE INVENTION

The present invention relates generally to systems and methods for stabilizing fractured long bones, such as a fracture of the distal femur.

BACKGROUND OF THE INVENTION

Trauma to the diaphyseal segment or the distal segment of the femur may result in simple or complex fractures that require treatment by surgical means. Typically, a metal pin or plate is used to reduce the fracture and stabilize the bone while healing occurs.

Figure 1:
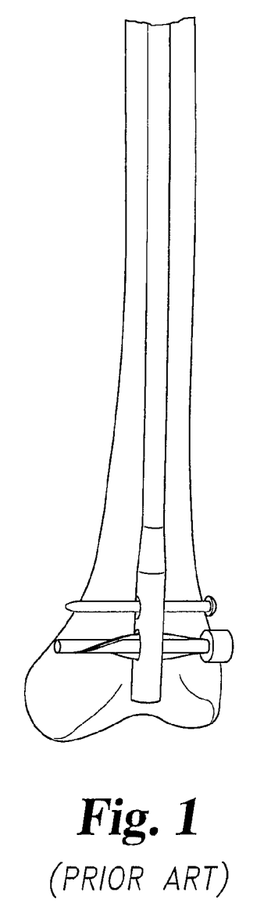
FIG. 1 shows a prior art intramedullary nail system.

For example, one method of treating distal femur fractures utilizes an intramedullary nail (or, alternatively, an IM pin or rod) which is inserted into the bone marrow canal and span a fracture in the bone. Such IM nails are designed to share the load with the bone and to assist with aligning and stabilizing the bone. In some such IM nail systems one or more screws or bolts are used to prevent movement of the nail with respect to the bone in an attempt to maintain proper alignment while the fracture heals. Most commonly, one screw or bolt is positioned below the fracture (near the distal end of the bone), while another screw or bolt may be positioned above the fracture. FIG. 1 shows an illustrative prior art intramedullary nail system.

Figure 2:
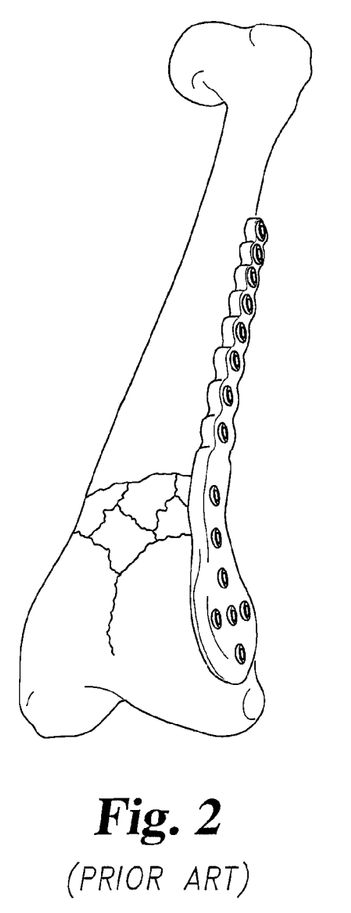
FIG. 2 shows a prior art locked plate system.
Figure 3:
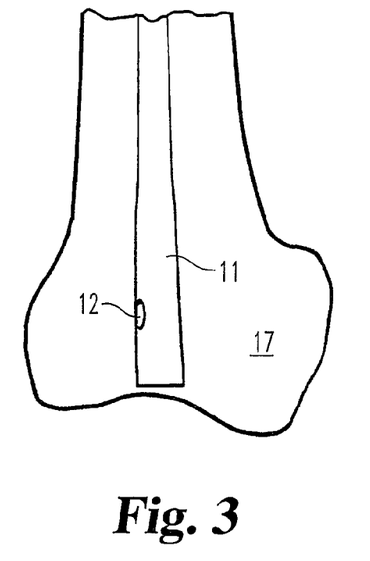
FIG. 3 shows an intramedullary nail as implanted in one embodiment of the present invention.

Alternatively, locked plate systems have been used to treat bone fractures. Such locked plate systems typically comprise a plate that lies outside and against the bone, with at least two clusters of bone screws passing through holes in the plate and into the bone. One of the screw clusters attaches to the bone above the fracture, while another screw cluster attaches to the bone below the fracture. At least some of the holes in the plate are threaded, and at least some of the bone screws have threaded "heads" that engage the threaded plate holes to "lock" the screws to the plate. When the screws are tightened the plate is "locked" to the bone above and below the fracture, thus providing the desired fracture reduction and stabilization. FIG. 2 shows an illustrative prior art locked plate fixation system.

Neither the prior art intramedullary nail systems nor the prior art locked plate systems provide an optimal fixation system for many long bone fractures. While the intramedullary nail systems may be relatively easy to use, the reduction and stabilization they provide may not be optimal since the nail typically has limited contact with the distal portion of the bone. While locked plate systems may provide improved contact with the bone, they may be difficult to align and are generally less easy to use. Additionally, locked plate systems have a biomechanical disadvantage since they are offset relative to the axis of the bone they are attempting to stabilize.

It can be seen from the above that a need exists for improved methods and devices to secure distal fixation of long bones that allows for early functional range of motion without loss of alignment or fixation. The present invention addresses that need.

SUMMARY OF THE INVENTION

In one aspect of the present invention there is provided a method of stabilizing a fractured bone, and particularly a long bone such as a femur, in a medical patient. The method generally comprises:
  a) providing a first structural support member in a medullary canal of a fractured bone;
  b) providing a second structural support member outside said fractured bone;
  c) providing a transverse connector adapted to link said first structural support member to said second structural support member in an angle-stable connection;
  d) connecting said transverse connector to said first structural support member in an angle-stable connection;
  e) connecting said transverse connector to said second structural support member in an angle-stable connection;
  f) providing one or more bone screws adapted to be connected to said second support member in an angle-stable connection;
  g) implanting said bone screws such that at least a portion of the shank of said bone screws is implanted in said fractured bone, and said bone screw is connected to said second support member in an angle-stable connection.

In one embodiment of this first aspect of the invention the first structural support member is an intramedullary nail and the second structural support member is a locking plate. The intramedullary nail may have a radial aperture adapted to receive the transverse connector.

One preferred embodiment of this first aspect of the invention may be characterized as follows:
  a) providing an intramedullary nail having a first aperture passing radially through the nail and adapted to receive a transverse connector and to hold said transverse connector in an angle-stable connection, and implanting said intramedullary nail in a fractured long bone;
  b) providing a locking plate having a first aperture adapted to receive a transverse connector in an angle-stable connection, and a second aperture adapted to receive a bone screw in an angle-stable connection, and positioning said locking plate against the outside surface of said fractured long bone;
  c) providing a first transverse connector having a head-end and a shank, said head-end being adapted to be received in the first aperture of said locking plate in an angle-stable connection, and said shank being adapted to be received by said radial aperture of said intramedullary nail,
  d) providing a bone screw having a head-end adapted to be received in the second aperture of said locking plate in an angle-stable connection;
  e) driving said first transverse connector through said first aperture in the locking plate, through at least a portion of the fractured bone, and through said radial aperture of said intramedullary nail;
  f) connecting said head-end of said first transverse connector to said locking plate in an angle-stable connection;
  g) connecting said shank of said first transverse connector to said intramedullary nail in an angle-stable connection; and
  h) driving said bone screw through said second threaded aperture in said locking plate and into said long bone without passing through said intramedullary nail; and
  i) connecting the head-end of said bone screw to said locking plate in an angle-stable connection.

In other preferred embodiments of this first aspect of the present invention the intramedullary nail includes a second aperture passing axially into the nail adjacent the radial aperture and adapted to receive a locking screw to assist in locking the transverse connector to the nail.

In other preferred embodiments of this first aspect of the present invention the first aperture of the locking plate is a threaded aperture adapted to receive a threaded head-end of a transverse connector.

In other preferred embodiments of this first aspect of the present invention the second aperture of the locking plate is a threaded aperture adapted to receive a threaded head-end of a bone screw.

In a second aspect of the present invention there is provided an apparatus for stabilizing a fractured long bone in a medical patient. The apparatus comprises:
  a) a first structural support member adapted to be implanted in a medullary canal of a fractured bone;
  b) a second structural support member adapted to be implanted outside said fractured bone;
  c) a transverse connector adapted to link said first structural support member to said second structural support member in an angle-stable connection; and
  d) one or more bone screws adapted to be connected to said second support member in an angle-stable connection.

In one embodiment of this second aspect of the invention the first structural support member is an intramedullary nail and the second structural support member is a locking plate.

In one preferred embodiment of this second aspect of the invention the intramedullary nail has a first aperture passing radially through the nail and adapted to receive a transverse connector in an angle-stable connection.

In another embodiment of this second aspect of the invention the second structural support member is a locking plate having a first aperture adapted to receive a transverse connector in an angle-stable connection, and a second aperture adapted to receive a bone screw in an angle-stable connection.

In another embodiment of this second aspect of the invention the transverse connector has a head-end and a shank, with the head-end being adapted to be received in the first aperture of said locking plate in an angle-stable connection, and the shank being adapted to be received by said radial aperture of said intramedullary nail in an angle-stable connection.

When implanted, the apparatus forms a four-part locked system wherein the plate is locked to the intramedullary nail through the transverse connector, and is further locked to the bone with locked bone screws. The system provides superior fixation of long bones that allows for early functional range of motion without loss of alignment or fixation.

DESCRIPTION OF THE PREFERRED EMBODIMENTS

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As indicated above, one aspect of the present invention relates to an assembly and method for stabilizing a fractured bone in a medical patient. The bone may be in a human or animal patient. Representative bones that may be treated by the inventive method include the femur, humerus, tibia, and ulna, with fractures of the distal femur being particularly appropriate for treatment by the inventive system and methods.

The inventive system and methods find particular utility for treating fractures to the diaphyseal segment or the distal segment of the femur. Use in other bones, or potentially in other segments of a femur, may also be appropriate depending on the specifics of the case. For example, the system and methods of the present invention may be employed in hindfoot fusion cases, where it may be desired to fuse from the calcaneus through the talus into the tibia.

The inventive assembly includes a first structural support member adapted to be implanted in a medullary canal of a fractured bone, a second structural support member adapted to be implanted outside said fractured bone, a transverse connector adapted to link said first structural support member to said second structural support member in an angle-stable connection, and one or more bone screws adapted to be connected to said second support member in an angle-stable connection. The components are linked together to provide a four-part construct that locks together in angle-stable connections. That is, the first structural support member in the medullary canal of a fractured bone is linked to the second structural support member outside the fractured bone by means of a transverse connector that connects the two structural support members together in an angle-stable connection. The bone screws are similarly linked to the second support member in an angle-stable connection, so that all four elements of the construct are locked together and loads are shared among the four components.

As indicated above, the first structural support member is preferably an intramedullary nail. The intramedullary nail may be of any size and diameter appropriate to stabilize the fracture of a particular medical patient. It is anticipated that the inventive method will find great utility with reducing and stabilizing fractures of the human femur, and for such applications nails having a diameter of between 9 mm and 15 mm, and a length of between 240 mm and 480 mm, are commonly used.

The intramedullary nail may have at least one aperture passing radially through the nail to receive the transverse connector and to hold it in an angle-stable connection. The radial aperture may be unthreaded, and may be sized to receive the transverse connector that connects the locking plate to the nail. Such an aperture may be round, or it may be oblong or another shape. In some embodiments a round aperture having a diameter of about 5 mm is used.

At least one threaded aperture passing axially into the nail adjacent the radial aperture(s) may also be provided in the nail. The axial aperture may be threaded to receive a set (locking) screw, and may be positioned adjacent to the radial aperture to allow the set/locking screw to be used to lock a transverse connector that passes through the radial aperture. The set screw used in the axial aperture may be threaded to match the threads of the axial aperture to allow the screw to be tightened against the radial aperture, thus locking the transverse connector to the nail.

It is to be appreciated that neither the radial aperture, nor the axial aperture, nor the locking screw are required in alternative embodiments of the first structural support member of the present invention, as long as an alternative structure is provided to allow the transverse connector to be "locked" to the support (e.g., the nail) in an angle-stable connection.

The second element of the inventive system is a structural support that will be positioned on the outside of the fractured bone. In one embodiment this support is a locking plate. The locking plate is adapted to be placed on the outside of the bone to stabilize the fracture when connected to the intramedullary nail via one or more transverse connectors, and is also adapted to engage bone screws that further stabilize the device.

The locking plate may include a plurality of threaded apertures to receive the threaded heads of bone screws and the transverse connector(s), and to hold the same in an angle-stable connection. As with the first structural support member though, threaded apertures are not required in embodiments that have alternative structures effective for "locking" the transverse connector and/or the bone screws to the locking plate in an angle-stable connection. Additional threaded or unthreaded apertures may also be provided in the locking plate.

The third element of the inventive system is the transverse connector(s). These connectors preferably have shanks effective for passing through the fractured bone ands connecting to the first structural support member (e.g., the nail), and "head" portions effective for connecting the nail to the locking plate in an angle-stable connection.

The shank(s) of the transverse connector(s) is adapted to span the distance between the first structural support member (e.g., the nail) and the second structural support member (e.g., the locking plate) and to lock those two components together in an angle-stable connection. An appropriate shank length is selected according to the size of the bone and the patient, with shank lengths of between 50 mm and 100 mm being appropriate for may adult patients when the system is implanted in a femur. Shank diameters of 4 mm to 7 mm are preferably used.

The shank of the connector may be roughened to facilitate locking the connector to the nail in an angle-stable connection. In some embodiments the shank(s) of the transverse connector(s) are "roughened" by providing a threaded shank, which may additionally facilitate driving the connector through the bone.

The "head" or "head-end" portion of the transverse connector(s) may include threads effective for locking the connector to a locking plate via a threaded aperture in the plate. Such threads may be provided in the literal "head" of the connector, or they may be provided in the portion of the shank that abuts the head of the connector. In either case the "head-end" of the transverse connector is threaded to engage threaded apertures in the locking plate. When the threaded head-end of the connector is locked into the locking plate and the shank of the connector is locked to the intramedullary nail with a set (locking) screw, the locking plate/connector/nail assembly provides a locked construct effective to stabilize a fractured long bone. As indicated above though, threads are not required in embodiments that have alternative structures effective for "locking" the transverse connector to the locking plate in an angle-stable connection.

The final element of the inventive system is the bone screws. Such bone screws are adapted to connect to the second structural support (the locking plate) in an angle-stable connection. In one embodiment the bone screws may have threaded heads to engage threaded apertures in the locking plate.

The bone screws are sized according to the specific surgical use, with screws having a diameter of 4 mm to 7 mm, and a length of 14 mm to 100 mm, being most commonly employed. Self-tapping cancellous and/or cortical screws are preferred for some applications. As with the transverse connectors, in some embodiments the literal "head" of the screw is not threaded, with the threads for engaging the locking plate residing in the upper portion of the screw shank where the shank abuts the literal screw head.

It is to be appreciated that the components used in the assembly may be made of any biocompatible material having sufficient strength to stabilize a fractured bone in a human or animal patient. Most preferably the assembly will be made of titanium or stainless steel.

To generally describe the method of using the bone fixation system of the present invention, the first structural support member (for example, an intramedullary nail) is implanted in a patient in the bone marrow canal of a long bone. The second structural support member (for example, a locking plate) is positioned on the outside surface of the bone. The transverse connector (which may have a threaded head) is used to connect the first structural support member to the second structural support member in an angle-stable connection. More particularly, the transverse connector may be driven through a threaded aperture of the locking plate, through the fractured bone, and through the unthreaded radial aperture of the intramedullary nail. The threaded head of the transverse connector may then be tightened to lock the connector to the locking plate. An axial locking screw is screwed into the threaded axial aperture of the intramedullary nail to lock the shank of the transverse connector to the nail. One or more bone screws are screwed through additional threaded apertures of the locking plate and into the long bone without passing through the intramedullary nail.

It is to be appreciated that the transverse connector connects the first structural support member (e.g., the nail) to the second structural support member (e.g., the locking plate) in an angle-stable connection. Such as connection may be referred to as a "locked" connection, and generally indicates that the two elements are not free to twist or rotate relative to each other. This "locking" feature makes the construct more stable than the systems of the prior art, and provides superior stabilization as forces are efficiently shared and transferred throughout the construct.

More particularly describing the preferred embodiments of the present invention with reference to the Figures, a first structural support member such as an intramedullary nail 11 is implanted in the bone marrow canal of a bone 17 of a human or animal patient, as shown generally in FIG. 1. In the illustrated embodiment the bone 17 is a human femur, although the inventive method may be used to reduce and stabilize other long bone fractures. In the illustrated embodiment a radial aperture 12 is provided in nail 11 to receive a transverse connector. An axial aperture 13 having threads 15 may be provided in nail 11 adjacent radial aperture 12.

Figure 4:
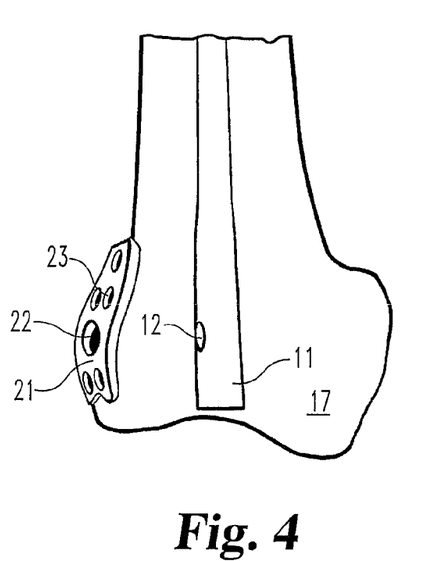
FIG. 4 shows a locking plate as positioned in one embodiment of the present invention.

A second structural support member such as a locking plate 21 is positioned on the outside of the bone, as illustrated in FIG. 4. At least one threaded aperture 22 sized to receive a transverse connector may be provided in locking plate 21, as may be additional threaded apertures 23 sized to receive bone screws.

Figure 5:
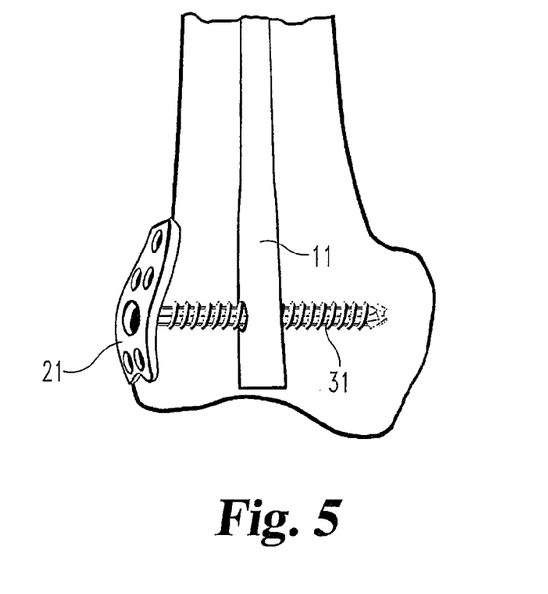
FIG. 5 shows a transverse connector as used in one embodiment of the present invention.

A transverse connector 31 is driven through aperture 22, through the bone 17, and through radial aperture 12 of nail 11 as illustrated in FIG. 5. When the locking plate has threaded apertures to receive and lock the transverse connector in an angle-stable connection, the connector 31 may be screwed tight so that the threaded head-end portion 35 of connector 31 engages the threads 25 of the threaded aperture 22 of locking plate 21, thus locking connector 31 to locking plate 21.

Figure 6:
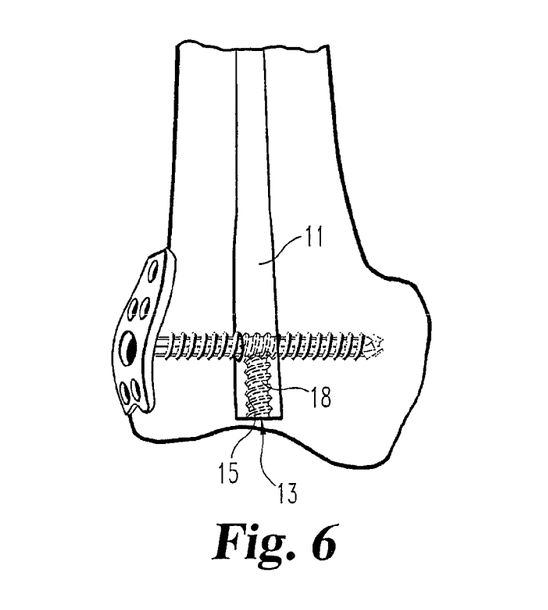
FIG. 6 shows an axial locking screw locking a transverse connector to the intramedullary nail of one embodiment of the present invention.
Figure 7:
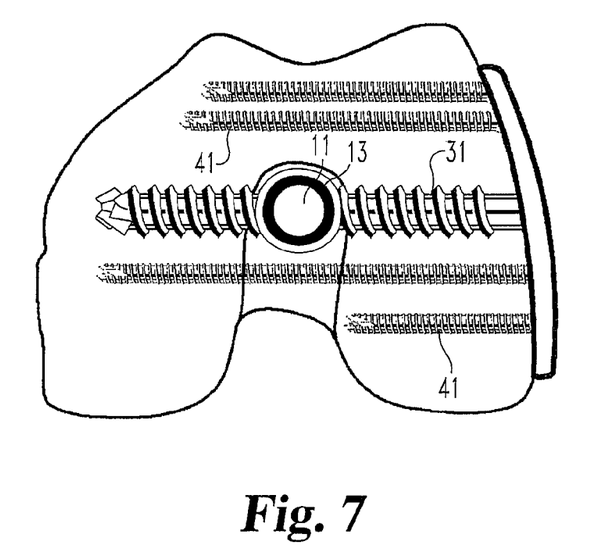
FIG. 7 shows an end view of a femur having a locking plate and a transverse connector locked to an intramedullary nail according to one embodiment of the present invention.

A locking screw 18 may be driven into axial aperture 13 of nail 11 so that locking screw 18 locks onto the surface of transverse connector 31, as illustrated in FIG. 6. When connector 31 has a roughened surface, such as the illustrated threaded surface, the locking screw may deform the surface of the connector to securely lock connector 31 to nail 11. An end view of the construct showing set screw 13 engaging transverse connector 31 is provided as FIG. 7.

Figure 8:
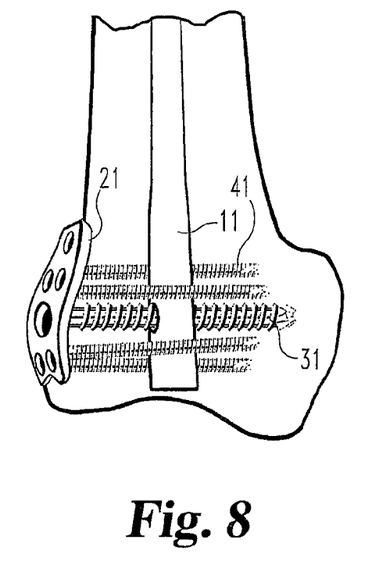
FIG. 8 shows locking bone screw as used in one embodiment of the present invention.

One or more bone screws 41 are driven through apertures 23 of locking plate 21 to engage bone 17, as illustrated in FIG. 8. These bone screws preferably have threaded head-ends to engage threaded apertures in the locking plate, thus allowing the bone screws to further lock the plate to the bone.

Figure 9:
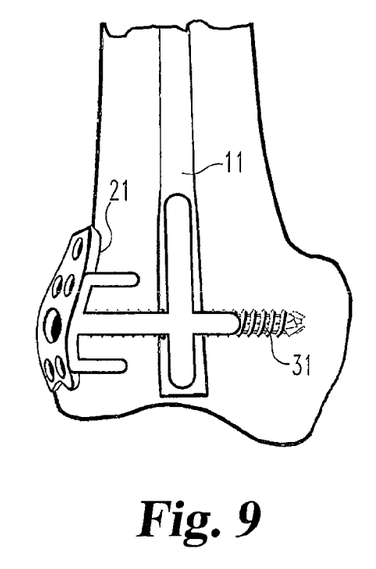
FIG. 9 shows the locked construct wherein the locking plate is locked to the intramedullary nail of one embodiment of the present invention.

The assembly provides a locked construct in which nail 11 is locked to connector 31 and locking plate 21 as illustrated in FIG. 9. When the nail is locked to the plate via locked transverse connectors, and when the plate is locked to the bone via locking bone screws, the construct forms a four-part locked system that provides superior fixation of long bones that allows for early functional range of motion without loss of alignment or fixation.

Figure 10:
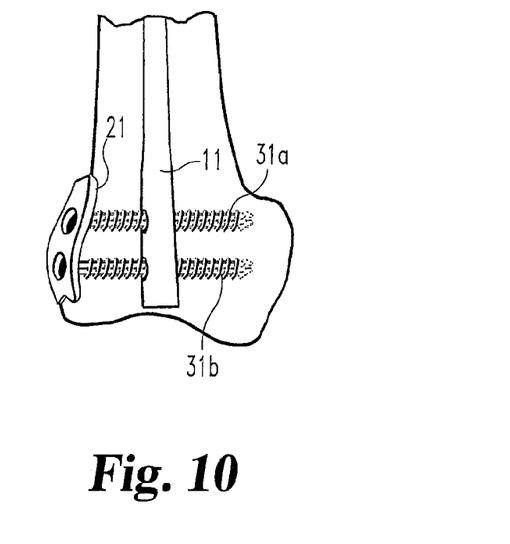
FIG. 10 shows an embodiment in which two transverse connectors are used to connect the locking plate to the intramedullary nail of the present invention.
Figure 11:
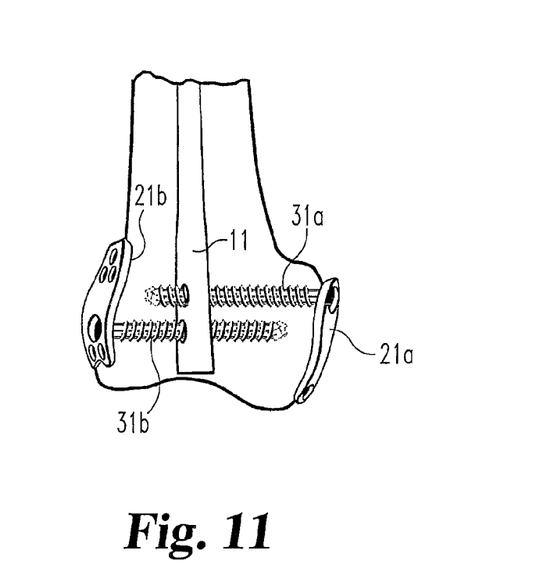
FIG. 11 shows an embodiment in which two locking plates and two transverse connectors are locked to the intramedullary nail of the present invention.
Figure 12:
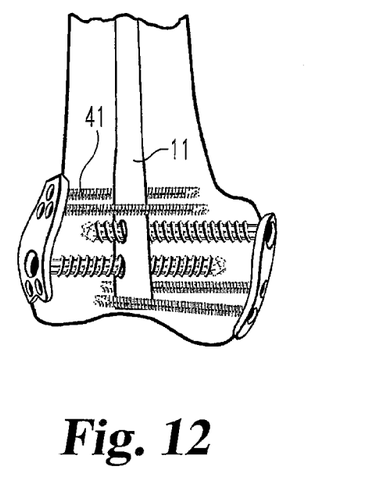
FIG. 12 shows another embodiment in which two locking plates and two transverse connectors are locked to the intramedullary nail of the present invention.

In alternative embodiments two or more transverse connectors 31a and 31b may be used to connect locking plate 21 to nail 11, as illustrated in FIG. 10. Similarly, two or more locking plates 21a and 21b may be used with multiple connectors 21a and 21b, as illustrated in FIG. 11. Such multiple locking plates 21a and 21b are preferably each provided with threaded apertures 23 to cooperate with multiple bone screws 41, as illustrated in FIG. 12.

It is to be appreciated that the assembly may be implanted using either a retrograde or an antegrade approach. Guides, reamers, and other devices to facilitate implantation of the various components may be used as would be appreciated by persons skilled in the art.

While the invention has been illustrated and described in detail in the drawings and foregoing description, the same are to be considered as illustrative and not restrictive in character, it being understood that only certain preferred embodiments have been shown and described, and that all changes and modifications that come within the spirit of the invention are desired to be protected.

What is claimed is:

1. An assembly for reducing and stabilizing a fracture in a long bone, comprising:
   a) an intramedullary nail having at least one radial aperture passing radially through the nail and adapted to receive a transverse connector in a locked, stable connection, and at least one axial aperture passing axially into the nail and adapted to receive a locking screw in a locked, stable connection;
   b) a first locking plate having a first aperture adapted to receive a transverse connector in a locked, stable connection, and a second aperture adapted to receive a bone screw in a locked, stable connection;
   c) at least one transverse connector having a head-end and a shank, the head-end being adapted to be received in the first aperture of said locking plate in a locked, stable connection, and the shank being adapted to be received in a radial aperture of said intramedullary nail in a locked, stable connection;
   d) at least one bone screw having a head-end adapted to fit an aperture of said locking plate in a locked, stable connection; and
   e) a locking screw adapted to fit in the axial aperture of said intramedullary nail, and effective for locking the shank of a transverse connector to the intramedullary nail.

2. The assembly of claim 1 wherein said transverse connector has a roughened shank.

3. The assembly of claim 1 wherein said transverse connector has a threaded shank.

4. The assembly of claim 1 wherein said locking plate includes at least three apertures, and wherein said assembly includes at least two bone screws adapted to be screwed into a long bone and locked in said plate.

5. The assembly of claim 1 wherein said intramedullary nail has at least two radial apertures passing radially through the nail; wherein said first locking plate has two apertures adapted to receive a head-end of a bone implant; and wherein the assembly includes two transverse connectors, wherein each of said transverse connectors has a head-end adapted to fit an aperture of said first locking plate and is sized to pass through an aperture in the locking plate, through at least a portion of the fractured bone, and through a radial aperture of said intramedullary nail.

6. The assembly of claim 1 wherein the assembly includes a second locking plate having a first aperture adapted to receive a transverse connector in a locked, stable connection, and a second aperture adapted to receive a bone screw in a locked, stable connection; and wherein said intramedullary nail has at least two radial apertures passing radially through the nail; and wherein each of said locking plates has at least three apertures adapted to receive a head-end of a bone implant; and wherein the assembly includes at least two transverse connectors, wherein each of said transverse connectors has a head-end adapted to fit an aperture of one of said locking plates and is sized to pass through an aperture in the locking plate, through at least a portion of the fractured bone, and through a radial aperture of said intramedullary nail.

* * * * *